US012582730B2

(12) United States Patent
Ebihara et al.

(10) Patent No.: US 12,582,730 B2
(45) Date of Patent: Mar. 24, 2026

(54) ELECTROPORATION DEVICES AND METHODS

(71) Applicant: Mayo Foundation for Medical Education and Research, Rochester, MN (US)

(72) Inventors: Hideki Ebihara, Rochester, MN (US); Jason A. Tri, Rochester, MN (US); Kalpathi L. Venkatachalam, Jacksonville Beach, FL (US); Paul A. Friedman, Rochester, MN (US); Christopher V. DeSimone, Rochester, MN (US); Daniel C. DeSimone, Rochester, MN (US); Martin van Zyl, Rochester, MN (US); Adetola O. Ladejobi, Rochester, MN (US); Andrew D. Badley, Rochester, MN (US); Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 688 days.

(21) Appl. No.: 17/918,160

(22) PCT Filed: Apr. 12, 2021

(86) PCT No.: PCT/US2021/026854
§ 371 (c)(1),
(2) Date: Oct. 11, 2022

(87) PCT Pub. No.: WO2021/211438
PCT Pub. Date: Oct. 21, 2021

(65) Prior Publication Data
US 2023/0139966 A1 May 4, 2023

Related U.S. Application Data

(60) Provisional application No. 63/009,342, filed on Apr. 13, 2020.

(51) Int. Cl.
| | |
|---|---|
| *A61M 16/04* | (2006.01) |
| *A61L 2/03* | (2006.01) |
| *A61M 1/34* | (2006.01) |

(52) U.S. Cl.
CPC ............. *A61L 2/03* (2013.01); *A61M 1/3472* (2013.01); *A61M 16/0402* (2014.02)

(58) Field of Classification Search
CPC ............................ A61M 16/0402; A61L 2/03
See application file for complete search history.

(56) References Cited

U.S. PATENT DOCUMENTS

| | | | |
|---|---|---|---|
| 5,634,899 | A | 6/1997 | Shapland et al. |
| 5,865,787 | A | 2/1999 | Shapland et al. |

(Continued)

FOREIGN PATENT DOCUMENTS

| | | |
|---|---|---|
| DE | 102012025164 A1 | 6/2014 |
| DE | 102014010907 A1 | 1/2016 |

(Continued)

OTHER PUBLICATIONS

Cheng et al., "Organ-protective effect of angiotensin-converting enzyme 2 and its effect on the prognosis of COVID-19," J. Med. Virol., Jul. 2020, 92(7):726-730.

(Continued)

*Primary Examiner* — Kevin Joyner
(74) *Attorney, Agent, or Firm* — Fish & Richardson P.C.

(57) ABSTRACT

Devices and methods are described for disinfection of pathogenic organisms using pulsed DC field electroporation. For example, this disclosure describes disinfection of pathogenic organisms using pulsed DC field electroporation for (Continued)

lung infection treatment, blood infection treatment, sterilization, and respirators.

8 Claims, 7 Drawing Sheets

(56)                    References Cited

U.S. PATENT DOCUMENTS

| | | | |
|---|---|---|---|
| 6,264,975 | B1 | 7/2001 | Boucher, Jr. |
| 7,113,821 | B1 | 9/2006 | Sun et al. |
| 9,351,790 | B2 | 5/2016 | Zemel et al. |
| 10,828,462 | B2 | 11/2020 | Daniels et al. |
| 2009/0143761 | A1 | 6/2009 | Cantor et al. |
| 2009/0253714 | A1 | 10/2009 | Johnson et al. |
| 2012/0089078 | A1 | 4/2012 | Deem et al. |
| 2015/0182282 | A1 | 7/2015 | Zemel et al. |
| 2015/0328449 | A1 | 11/2015 | Soden et al. |
| 2017/0095628 | A1 | 4/2017 | Bartlett, II et al. |
| 2018/0296264 | A1 | 10/2018 | DeSimone et al. |
| 2019/0030328 | A1 | 1/2019 | Stewart et al. |
| 2019/0231425 | A1 | 8/2019 | Waldstreicher et al. |
| 2019/0282290 | A1 | 9/2019 | Wolf et al. |
| 2021/0146126 | A1 | 5/2021 | Waldstreicher et al. |
| 2022/0047686 | A1 | 2/2022 | Asirvatham et al. |

FOREIGN PATENT DOCUMENTS

| | | | |
|---|---|---|---|
| EP | 0785987 | B1 | 8/1999 |
| WO | WO 94/21117 | A1 | 9/1994 |
| WO | WO 2003/013615 | | 2/2003 |
| WO | WO 2007/046757 | A1 | 4/2007 |
| WO | WO 2017/173089 | A1 | 10/2017 |
| WO | WO 2018/005511 | | 1/2018 |
| WO | WO 2019/133606 | | 7/2019 |
| WO | WO 2023/076046 | A1 | 5/2023 |

OTHER PUBLICATIONS

Colalto, "Volatile molecules for COVID-19: A possible pharmacological strategy?," Drug Dev. Res., Dec. 2020, 81(8):950-968.

Klimke et al., "Hydroxychloroquine as an aerosol might markedly reduce and even prevent severe clinical symptoms after SARS-COV-2 infection," Med. Hypotheses, Sep. 2020, 142(109783):1-4.

Extended European Search Report in European Appln No. 21787717. 4, dated Aug. 14, 2023, 7 pages.

Al-Jumaili et al., "Review on the Antimicrobial Properties of Carbon Nanostructures," Materials, Sep. 2017, 10(9):1066, 26 pages.

International Preliminary Report on Patentability in International Appln. No. PCT/US2021/026854, mailed on Oct. 27, 2022, 6 pages.

International Search Report and Written Opinion in International Appln. No. PCT/US2021/026854, mailed on Sep. 1, 2021, 8 pages.

The New York Times [online], "As Coronavirus Looms, Mask Shortage Gives Rise to Promising Approach," Mar. 20, 2020, retrieved on Feb. 22, 2022, retrieved from URL<https://www.nytimes.com/2020/03/20/health/coronavirus-masks-reuse.html>, 3 pages.

Velebit et al., "Non-thermal inactivation of Noroviruses in food," Presented at Proceedings of the 59th International Meat Industry Conference MEATCON2017, Mt. Zlatibor, Serbia, Oct. 1-4, 2017; Conference Series: Earth and Environmental Science, Sep. 2017, 85(1):012021, 7 pages.

Viruses in Food, 2nd ed., Goyal et al. (eds.), Aug. 2016, Chapter 15, 27 pages.

Extended European Search Report in European Appln. No. 25175503. 9, mailed on Aug. 19, 2025, 8 pages.

500

520

520

510b

510a

530

1

ELECTROPORATION DEVICES AND METHODS

CROSS-REFERENCE TO RELATED APPLICATIONS

This application is a National Stage application under 35 U.S.C. § 371 of International Application No. PCT/US2021/026854, having an International Filing Date of Apr. 12, 2021, which claims the benefit of U.S. Provisional Application Ser. No. 63/009,342, filed Apr. 13, 2020. The disclosure of the prior applications are is considered part of (and are incorporated by reference in) the disclosure of this application.

BACKGROUND

1. Technical Field

This disclosure relates to devices and methods for disinfection of pathogenic organisms using pulsed DC field electroporation. For example, this disclosure relates to disinfection of pathogenic organisms using pulsed DC field electroporation for lung infection treatment, blood infection treatment, sterilization, and respirators.

2. Background Information

Protective masks exist in several types and form factors designed to prevent aerosol and aerosolized particles carrying pathogenic organisms including bacteria, fungi, and viruses from entering the respiratory track and in some instances worn by infected individuals to prevent dissemination. Some of the problems with existing masks are that they are not very effective for viruses and they inherently have gaps partly because of the fit on a person and partly because of the need for air exchange and normal breathing. Ideally, a mask should have easily changeable forms that do not impede air exchange at all even in its most restrictive form and be effective for a variety of pathogens including viruses by virtue of effects on protein coats or nucleic acids independent of membrane effects.

SUMMARY

This disclosure describes devices and methods for disinfection of pathogenic organisms using pulsed DC field electroporation. For example, this disclosure describes disinfection of pathogenic organisms using pulsed DC field electroporation for lung infection treatment, blood infection treatment, sterilization, and respirators.

In one aspect, this disclosure is directed to a system for treatment of lung infections of a patient. The system includes an endotracheal tube, a first electrode that is advanceable along the endotracheal tube, a second electrode configured for placement on an exterior chest wall of the patient, a source of particulate aerosols, the source configured to introduce the particulate aerosols into airways of the patient via the endotracheal tube; and a power source configured to deliver energy to the first electrode that causes the first electrode to emit pulse electroporation fields.

In another aspect, this disclosure is directed to a method for treating lung infections of a patient. The method includes: (i) advancing a first electrode along an endotracheal tube that is within a trachea of the patient; (ii) placing a second electrode on an exterior chest wall of the patient; (iii) introducing particulate aerosols into airways of the patient via the endotracheal tube; and (iv) delivering energy to the first electrode to cause the first electrode to emit pulse electroporation fields.

In some embodiments of the method, the pulse electroporation fields are at least partially propagated by the particulate aerosols.

In another aspect, this disclosure is directed to an electroporation respirator mask that includes a respirator mask including a porous material configured to cover a mouth and nose of a user, multiple electrodes attached to the respirator mask, and a power source configured to energize the electrodes so that the electrodes generate pulse electroporation fields.

Such a electroporation respirator mask may optionally include a one-way exhaust valve integrated with the porous material. The one-way exhaust valve may be reconfigurable between an open position and a closed position. The one-way exhaust valve may self-configure in the open position in response to exhalations of a user of the respirator mask and return to the closed position in response to inhalations of the user.

In another aspect, this disclosure is directed to an electroporation respirator that includes a frame configured to be worn on a user's head, multiple electrodes attached to the frame such that a space is defined between the multiple electrodes, and a power source configured to energize the multiple electrodes so that the electrodes generate pulse electroporation fields within the space.

In another aspect, this disclosure is directed to a blood treatment system that includes: (a) a blood product separator configured to receive blood and to separate the blood into components comprising: (i) blood containing cells and (ii) filtered plasma water containing viruses; (b) an electroporation chamber configured to receive the filtered plasma water containing viruses from the blood product separator and to output treated blood that has a decreased pathogenicity because of an electroporation treatment of the filtered plasma water containing viruses in the electroporation chamber; (c) a first pump configured to pump treated blood received from the electroporation chamber to the patient; and (d) a second pump configured to pump the virus-free filtered plasma water output from the blood product separator to the patient.

Particular embodiments of the subject matter described in this document can be implemented to realize one or more of the following advantages. First, some embodiments described herein allow the reuse of personal protective equipment (PPE) by sterilizing PPE at point of use. By reusing PPE, PPE shortages and scarcities are mitigated. In addition, consumption and associated costs of PPE are reduced.

Second, some respirator embodiments described herein do not impede air exchange to and from the user. Rather, users are allowed to breathe normally. Moreover, some individuals who are claustrophobic will feel less stressed using some respirator embodiments described herein.

Third, the devices and methods described herein can be used for sterilization of rooms, surfaces, and even airspaces such as entryways. Such sterilization is efficient and unobtrusive.

Fourth, devices and methods described herein provide electroporation therapeutics such as, but not limited to, treatment of lung infections including viral pneumonia. In addition, devices and methods described herein provide blood treatment to eliminate or inactivate viruses contained within the blood.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This disclosure describes devices and methods for disinfection of pathogenic organisms using pulsed DC field electroporation. For example, this disclosure describes disinfection of pathogenic organisms using pulsed DC field electroporation for lung infection treatment, blood infection treatment, sterilization, and respirators.

For example, such an electric field-based disinfection system may be used beyond protective headwear but for disinfection of existing masks to enable reusability, for use in air purification systems around in isolation rooms and buildings in general and as a potential treatment modality when infection has already occurred. The ability to reuse personal protective equipment (PPE) such as respirator masks and eye protection is especially important in pandemic situations where shortages arise or in normal everyday scenarios as a potential cost cutting measure.

Figure 1:
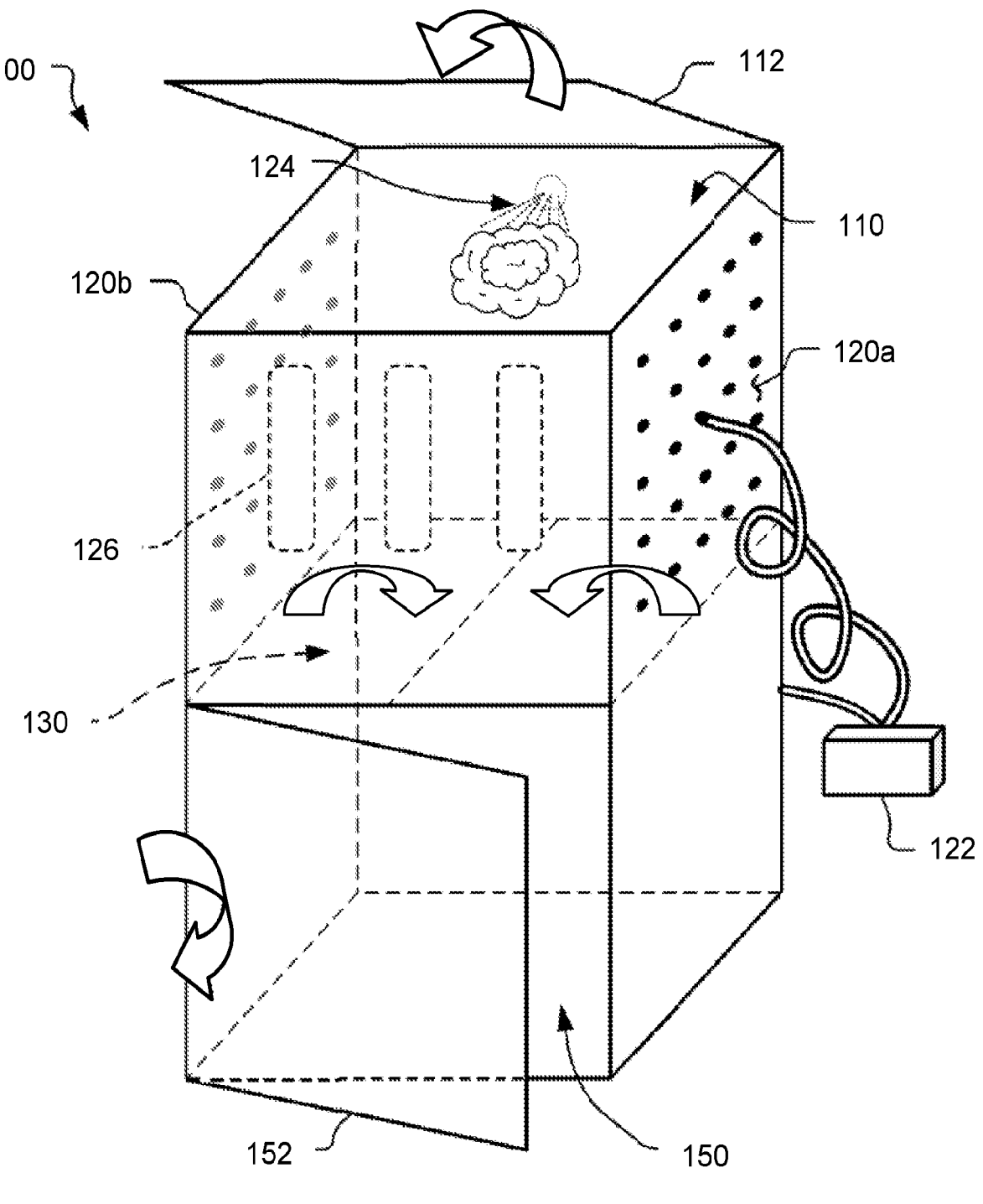
FIG. 1 is an isometric view of an example point of care PPE sterilization unit in accordance with some embodiments.

Referring to FIG. 1, items such as respirators can be sterilized in a point of care sterilization unit 100 and reused. In the depicted embodiment, the point of care sterilization unit 100 includes a first chamber 110 and a second chamber 150. Although not required, the first chamber 110 can be positioned above the second chamber 150 as depicted. A separator 130 is positioned between the first chamber 110 and the second chamber 150.

The first chamber 110, which is the sterilization chamber, can be accessed by opening a door 112. The second chamber 150, which is the sterilized PPE storage chamber, can be access by opening a door 152. The separator 130 is openable and closable. In the depicted embodiment, the separator 130 is configured like a trap door with two halves that swing apart from each other in a downward direction. In some embodiments, the separator 130 opens and closes automatically at the proper time of a sterilization process.

The point of care sterilization unit 100 can include one or more of the following features, in any combination, that can be used for sterilization of PPE. First, in some embodiments, the first chamber 110 includes multiple electrodes that can deliver electroporation energy (e.g., high-frequency pulsation of DC or AC field energy that can irreversibly destroy target cells). In the depicted embodiment, the first chamber 110 includes a first electroporation plate 120a and a second electroporation plate 120b. Each of the electroporation plates 120a-b can be replaced with one or more electroporation electrodes. In the depicted embodiment, each of the electroporation plates 120a-b participates in generating the pulsed electric fields used for electroporation. The point of care sterilization unit 100 can include a power source and control unit 122. The power source and control unit 122 can provide the power to the electroporation plates and can control the operation process of the point of care sterilization unit 100.

Second, in some embodiments the point of care sterilization unit 100 includes an aerosolized fluid source 124. The aerosolized fluid source 124 can inject aerosolized liquid (e.g., distilled water, saline, etc.) into the first chamber 110. The airborne aerosolized liquid can facilitate an increase in efficacy of the electroporation process described above. In some embodiments, the aerosolized fluid source 124 can be used to generate or inject a sterilization agent such as vaporized hydrogen peroxide into the first chamber 110.

Third, in some embodiments the point of care sterilization unit 100 includes one or more UV light sources 126. The one or more UV light sources 126 can project UV light energy into the first chamber 110 and thereby also increase the efficacy of the sterilization process of the point of care sterilization unit 100.

In some embodiments, the point of care sterilization unit 100 includes the first chamber 110 but not the second chamber 150. In such an embodiment, the separator 130 is simply configured as a singular bottom wall of the first chamber 110 (without being hinged like a trap door). Accordingly, point of care sterilization unit 100 is a single box (the first chamber 110) that can be accessed internally by opening the door 112. The door 112 may be on the top or a side of the first chamber 110.

While the depicted embodiment depicts the electroporation plates 120a-b as being the walls of the first chamber 110, or as being integrated into the walls of the first chamber 110, in some embodiments the electroporation plates 120a-b are placed within the first chamber 110 and separate from the walls. For example, in some embodiments the electroporation plates 120a-b can be mounted within the first chamber 110 using stand-offs from the walls of the first chamber 110. The space between the electroporation plates 120a-b can be used to position the items to be sterilized (such as respirators). In some embodiments, the electroporation plates 120a-b are each a single metallic plate that acts as a single large electrode.

The goal here is a point of care sterilization unit 100 that can be used in various clinical areas such as operating room, emergency departments, ICUS, etc. PPE needing sterilization can be put into the first chamber 110. The sterilization process can then be activated by a user. Sterilization of the PPE within the first chamber 110 will then take place for a predetermined period of time (which may be adjustable). When the sterilization phase is complete, the separator 130 can open and the sterile PPE can drop from the first chamber 110 into the second chamber 150. Then the separator 130 can close. Sterilized PPE will be staged in the second chamber 150 and can be accessed from the second chamber 150 when needed for use.

Accordingly, electroporation will be deployed within the point of care sterilization unit 100 to sterilize PPE (e.g., N95 masks, face shields, etc.) and thus promote reusability. At a high level, the electroporation can be used as the sole sterilizing agent in a chamber with ambient air or one into which aerosolized liquid (e.g. normal saline, distilled water, etc.) has been introduced. The aerosolized liquid can potentiate the effect of electroporation and prevent arcing. Furthermore, electroporation can be combined with other sterilization modalities such as vaporized hydrogen peroxide (VHP) and ultraviolet light (Ultraviolet C; UVC) to improve both the efficiency and efficacy of sterilization.

Regarding VPH, the point of care sterilization unit 100 can generate hydrogen peroxide by electroporation of water molecules contained in the aerosolized liquid. UVC can also help convert aerosolized water to VPH. With UVC, a UVC light source (pulsed or continuous) can be incorporated in the first chamber 110 that will then be coated with reflective material that will not significantly change the wavelength of reflected light. The reflective surface will allow the UV light to be distributed within the first chamber 110 while also preventing it from escaping outside of the first chamber 110. Materials within the first chamber 110 may be agitated either by rotating the first chamber 110 or by using an air stream or other mechanism to move materials around within the first chamber 110. Literature review suggests ultraviolet germicidal irradiation (UVGI) exposures as low as of 2-5 mJ/cm$^2$ are capable inactivating coronaviruses on surfaces but higher doses may be needed to penetrate all the layers of facemasks.

Other iterations of the principle of pulsed DC field for disinfection or antiviral therapy are also envisioned. For example, electrodes can be placed around doorways. The electrodes can emit low energy fields below the threshold for skeletal stimulation. In another embodiment, higher energy fields can be emitted from a form factor resembling a gun or similar tool directed by an individual or robot to cleanse surgical theaters, procedural rooms, or other areas of known or high at risk for viral or other pathogen contamination. These iterations may also include humidified and aerosolized fluid or be electrical fields alone. Specific times spent under such a field may produce absolute decontamination and may allow isolation of individuals despite being in large groups, for example, with the entire group going into a completely disinfected environment and going through a specified contact time with the pulsed field when leaving the group. One variation is to include an electrically conductive material or fine wires within the fabric of what appears to be a normal mask so there is no exposure by anyone to the electricity.

Figures 2, 3:
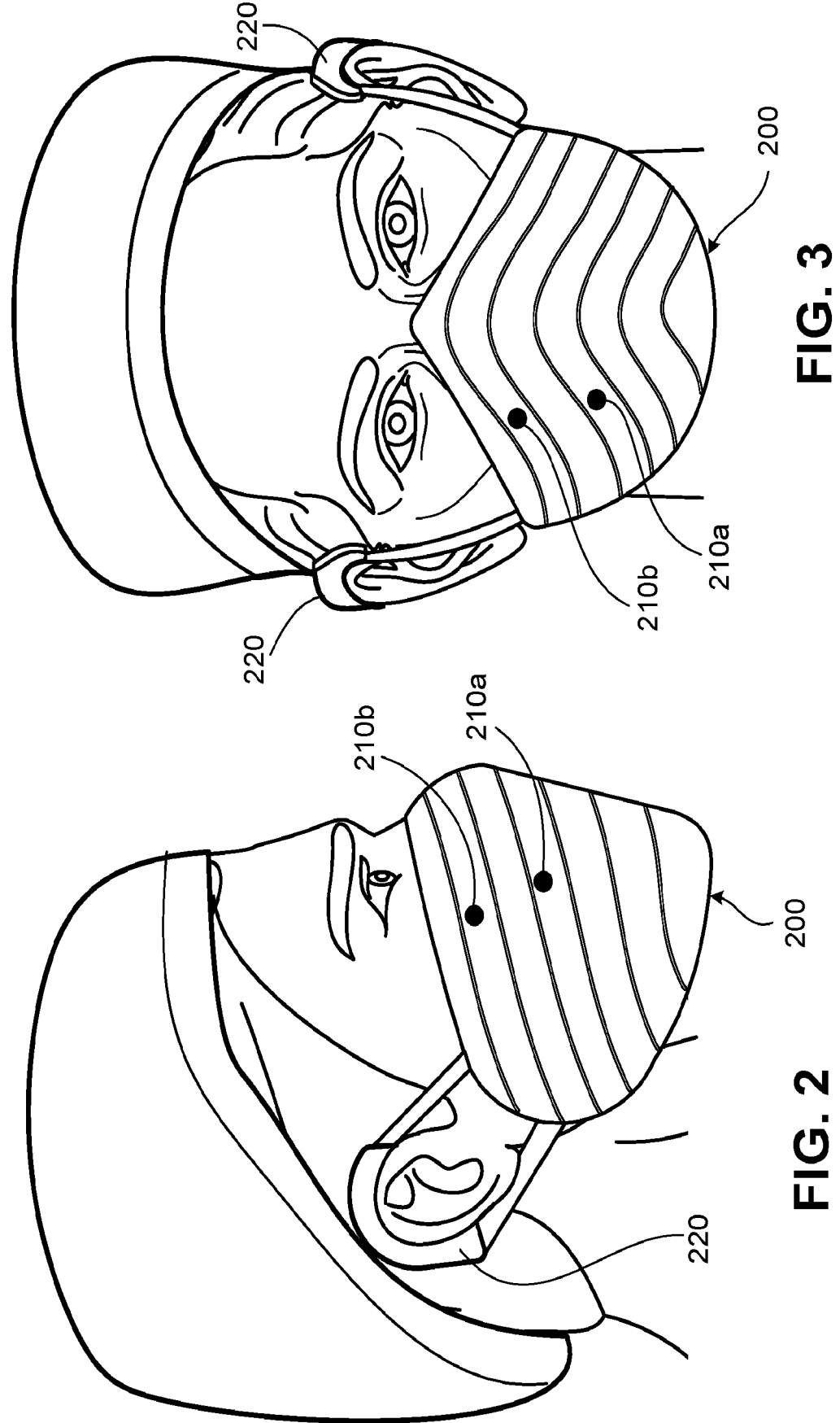
FIGS. 2 and 3 are views of an example electroporation respirator mask in accordance with some embodiments.

Referring to FIGS. 2 and 3, an example electroporation respirator mask 200 has the form and characteristics of existing masks but in addition has variably spaced electrodes 210a and 210b in the linings of the mask 200 that in turn are connected to a small pulsed electric field (PEF) generator 220 that may be detachable and small enough to place over the ears in a pocket, etc. Any number of electrodes may be included. The same circuitry could be used for overprotective eyewear or a combination of the eyewear and mask such as with a hood.

Pulsed DC fields delivered via these electrodes 210a-b would be insulated from the individual by the lining of mask 200 between the electrodes 210a-b and the person wearing the mask 200. In some embodiments, the electrodes 210a-b could be made of any suitable conductive material including, but not limited to, Mu metal, carbon nanotubes, and graphene or other suitable material. Incorporation into the mask 200 could be via nano-spinning or other viable methods.

In some embodiments, the spacing between the electrodes 210a-b can be adjusted. In particular embodiments, the mask 200 includes electrically conductive materials.

In some embodiments, in order to re-sterilize the mask 200, the mask 200 can be plugged into a stationary PEF generator while the mask 200 is not being worn. The electrodes 210a and 210b in the linings of the mask 200 will generate an electrical field that will irreversibly electroporate pathogenic organisms.

Figures 4, 5:
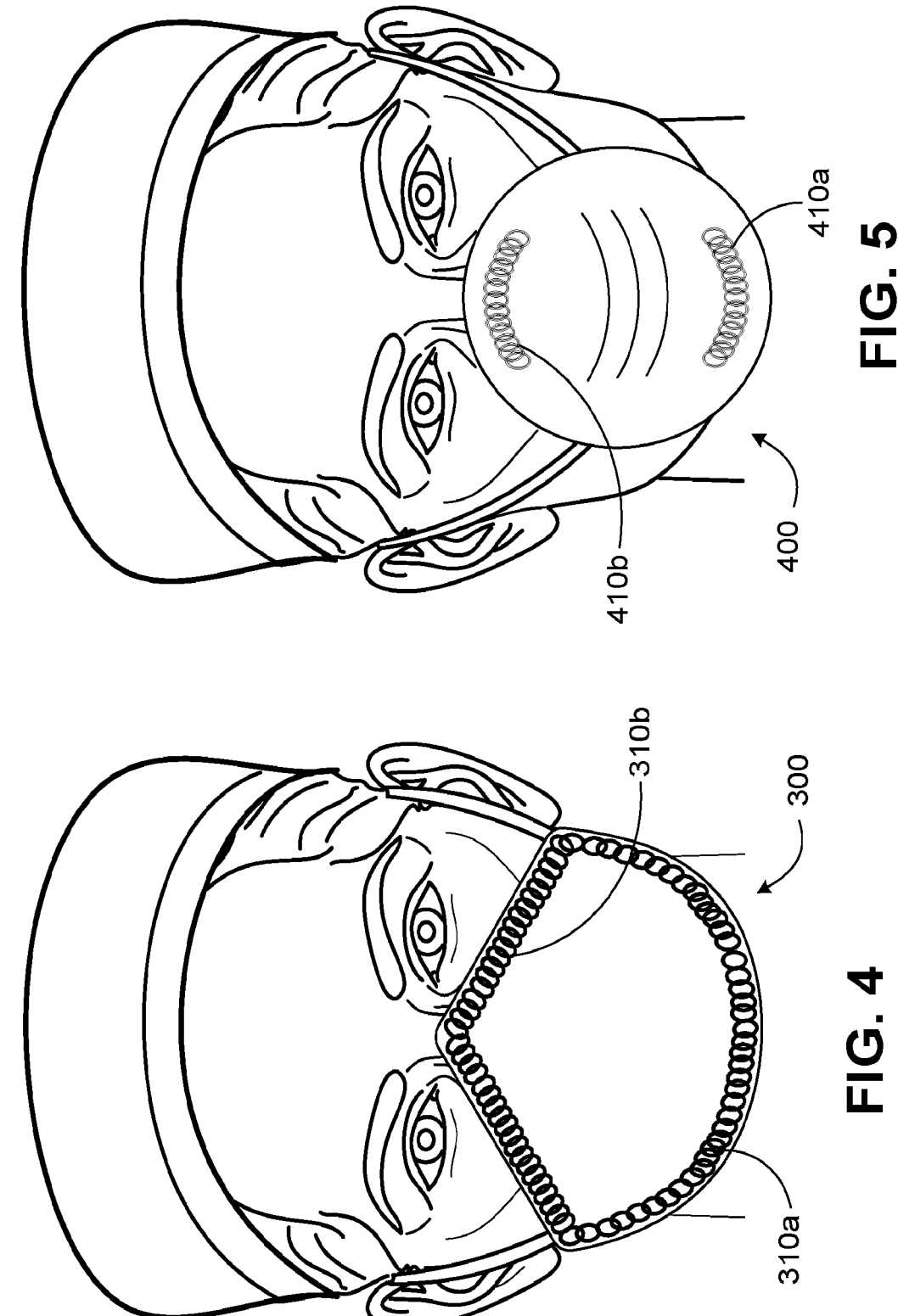
FIG. 4 shows another example electroporation respirator mask in accordance with some embodiments.
FIG. 5 shows another example electroporation respirator mask in accordance with some embodiments.

Referring to FIG. 4, another example respirator mask 300 can include electrodes 310a and 310b in the linings of the mask 300. In this case, multiple electrodes 310a-b are located along the edges of the mask 300. The electrodes 310a-b can be connected to a small PEF generator that may be detachable and small enough to place over the ears in a pocket, etc.

Referring to FIG. 5, another example respirator mask 400 (in this case an N95 style of mask) can include electrodes 410a and 410b in the linings of the mask 400.

In this case, multiple electrodes 410a-b are located along the edges of the mask 400. The electrodes 410a-b can be connected to a small PEF generator that may be detachable and small enough to place over the ears in a pocket, etc.

In some embodiments, the respirator masks 200, 300, and 400 can include a valve-like feature to make the user's breathing (exhaust) less restricted. In other words, in order to provide reduced restrictions for the user to breathe out (to exhale), in some embodiments the respirators 200, 300, and 400 can have an integrated one-way exhaust valve.

Such a one-way exhaust valve can have various forms. In one example, the one-way exhaust valve can be a flap made of porous respirator material. Such a flap can deflect outwardly (self-configure) to an open position in response to the increased air pressure inside the mask as the user exhales. The outward deflection can open up more free area for the exhausted air to leave the confines of the mask, making for less airflow resistance. Then, during inhalation, the flap can return to its closed position so that the air being inhaled by the user is ensured of passing through the mask material. During the exhaling while the flap is open, the exhaled air passes through the electrical field created by the electrodes. Accordingly, the electrical field created by the electrodes will irreversibly electroporate pathogenic organisms in the exhaled air that is passing through the one-way exhaust valve. This one-way exhaust valve feature present in some embodiments of the respirator masks 200, 300, and 400 can improve user comfort without sacrificing mask performance.

Figure 6:
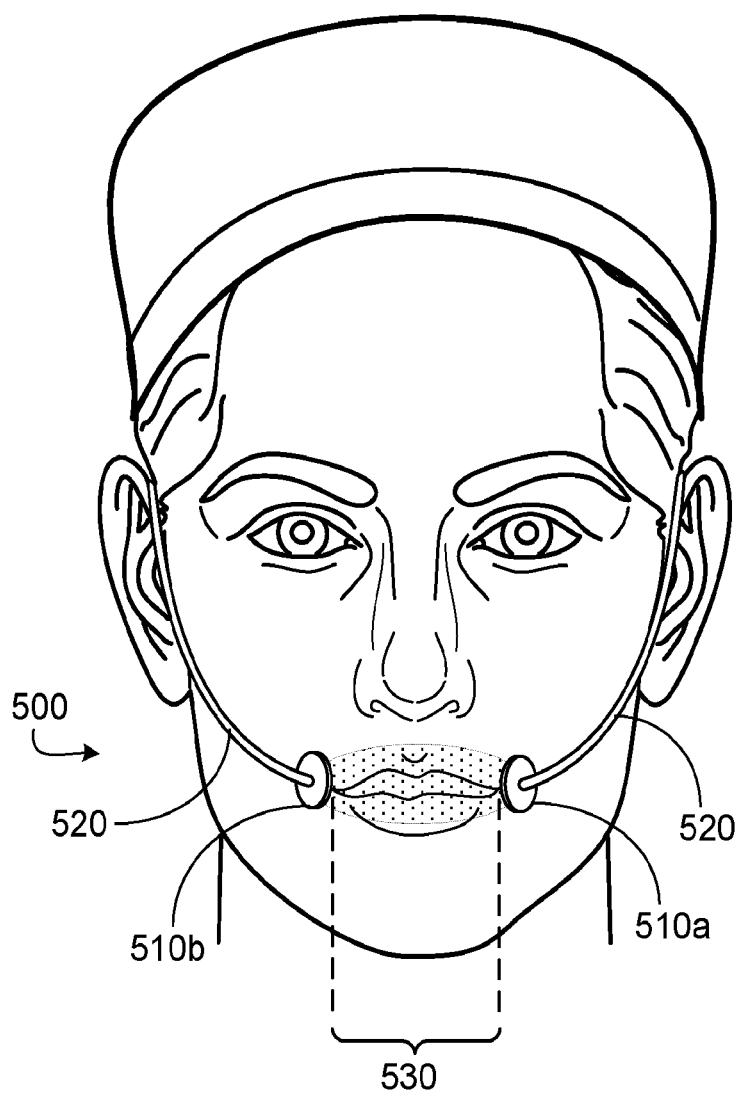
FIG. 6 shows an example electroporation respirator in accordance with some embodiments.

Referring to FIG. 6, another type of respirator 500 is depicted. The respirator 500 includes a first electrode node 510a and a second electrode node 510b. The first electrode node 510a and the second electrode node 510b are positionable on opposite sides of the user's mouth and/or nose. The electrodes 510a-b can be mounted to a frame 520 that can extend over the user's ears and around the back of the user's head. A space 530 is defined between the electrodes 510a-b.

In this iteration, there is no form or fabrication similar to existing masks but an electric field alone is generated between the electrodes 510*a-b* in the space 530. This design could also be worn solely around the ears, as a nose clip, as a collar, or as a cap. There is no obstruction to vision or breathing, but the pulsed field between the electrodes 510*a-b* will act as a disinfecting medium for all pathogens, potentially dust particles or allergens including viral particles.

Figures 7, 8:
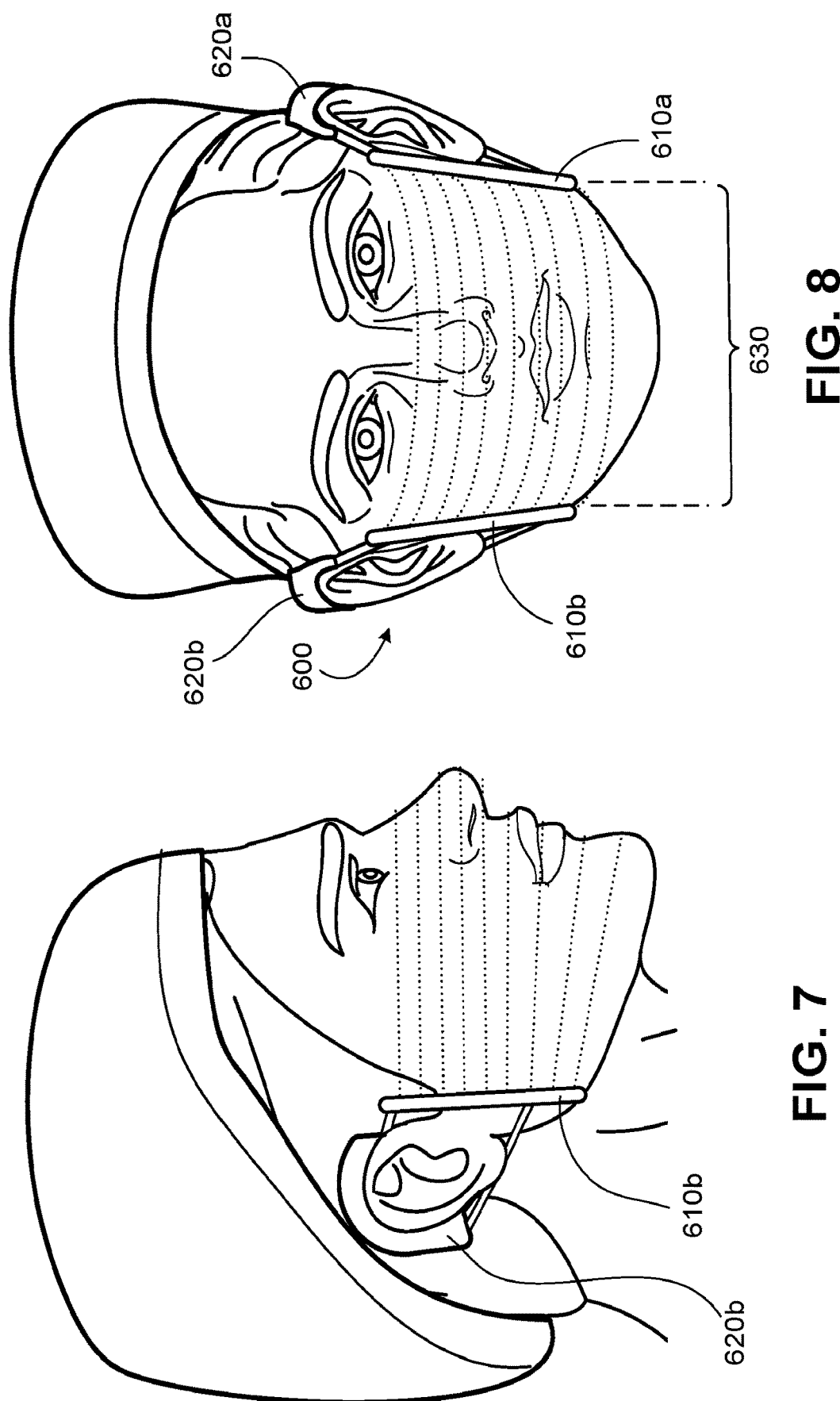
FIGS. 7 and 8 are views of another example electroporation respirator in accordance with some embodiments.

Referring to FIGS. 7 and 8, another type of respirator 600 is depicted. The respirator 600 includes a first elongate electrode bar 610*a* and a second elongate electrode bar 610*b*. The first electrode bar 610*a* and the second electrode bar 610*b* are positionable on opposite sides of the user's mouth and/or nose. A space 630 is defined between the electrode bars 610*a-b*. In this iteration, there is no form or fabrication similar to existing masks but an electric field alone is generated between the electrode bars 610*a-b* in the space 630. Any number of electrodes may be included.

This design could also be worn solely around the ears, as a nose clip, as a collar, or as a cap. There is no obstruction to vision or breathing, but the pulsed field between the electrode bars 610*a-b* will act as a disinfecting medium for all pathogens, potentially dust particles or allergens including viral particles.

In the depicted embodiment, the energy sources supplying the electrode bars 610*a-b* are a first PEF generator 620*a* and a second PEF generator 620*b*, respectively. The PEF generators 620*a-b* that may be detachable and small enough to wear on/over the ears, in a pocket, etc.

Electroporation Therapeutics

This disclosure is also directed to electroporation therapeutics such as, but not limited to, combined electrical fields for treatment of existing lung infections including viral pneumonia. In this embodiment, pulsed electrical fields along with aerosolized or humidified conducting or other particles is used as a treatment modality for pulmonary infections.

For example, in an intubated patient, the particulate aerosols are introduced into the airways of the patient through the endotracheal tube. One electrode is advanced in the endotracheal tube to the region of the carina or thereabouts, and the return electrodes are placed on the chest walls of both sides (assuming both lungs are infected).

Pulsed electroporation fields are given periodically at increasing doses while monitoring airway pressures. Once airway pressures show an effect (e.g., either by an increasing in the plateau or peak pressures), direct pulmonary effects may be presumed and the energy delivery stopped.

Available data suggests that bacterial cell walls are susceptible to very low pulsed energy levels, well-below what may be anticipated to cause direct or permanent pulmonary damage. Viral thresholds have not been established, but available data again suggests the mechanism of action should be at the protein coat the virus and have thresholds or frequencies significantly below permanent direct lung toxicity, for example, at levels of 1-20 kilovolts at 1 msec pulse or equivalent charge and current flow.

Further, in-vitro testing of pulsed field effects on individual viruses can be made with local resistivity calculated and a specific waveform or energy delivery sequence done to alter a particular pathogen including a particular virus without necessarily affecting other sites with nonpathogenic organisms or physiologic tissue. For non-intubated patients, the particulate matter might be aerosolized and delivered by a facemask with low energy pulses given across the chest field and without an electrode placed within the airways.

In another iteration for non-intubated patients who may not be fully sedated, the energy may be delivered to the lung fields via the vasculature, for example, bipolar or multipolar possibly multiphasic energy delivery via branches of the pulmonary artery for a given lung field. Actual delivery sequences and energy levels can be titrated for individual patients with modeling to anticipate magnitude of the field and ex-vivo testing for disinfection thresholds for individual organisms possibly done as a part of viral or bacterial cultures similar to what is done for antibiotic or antiviral testing presently.

Figure 9:
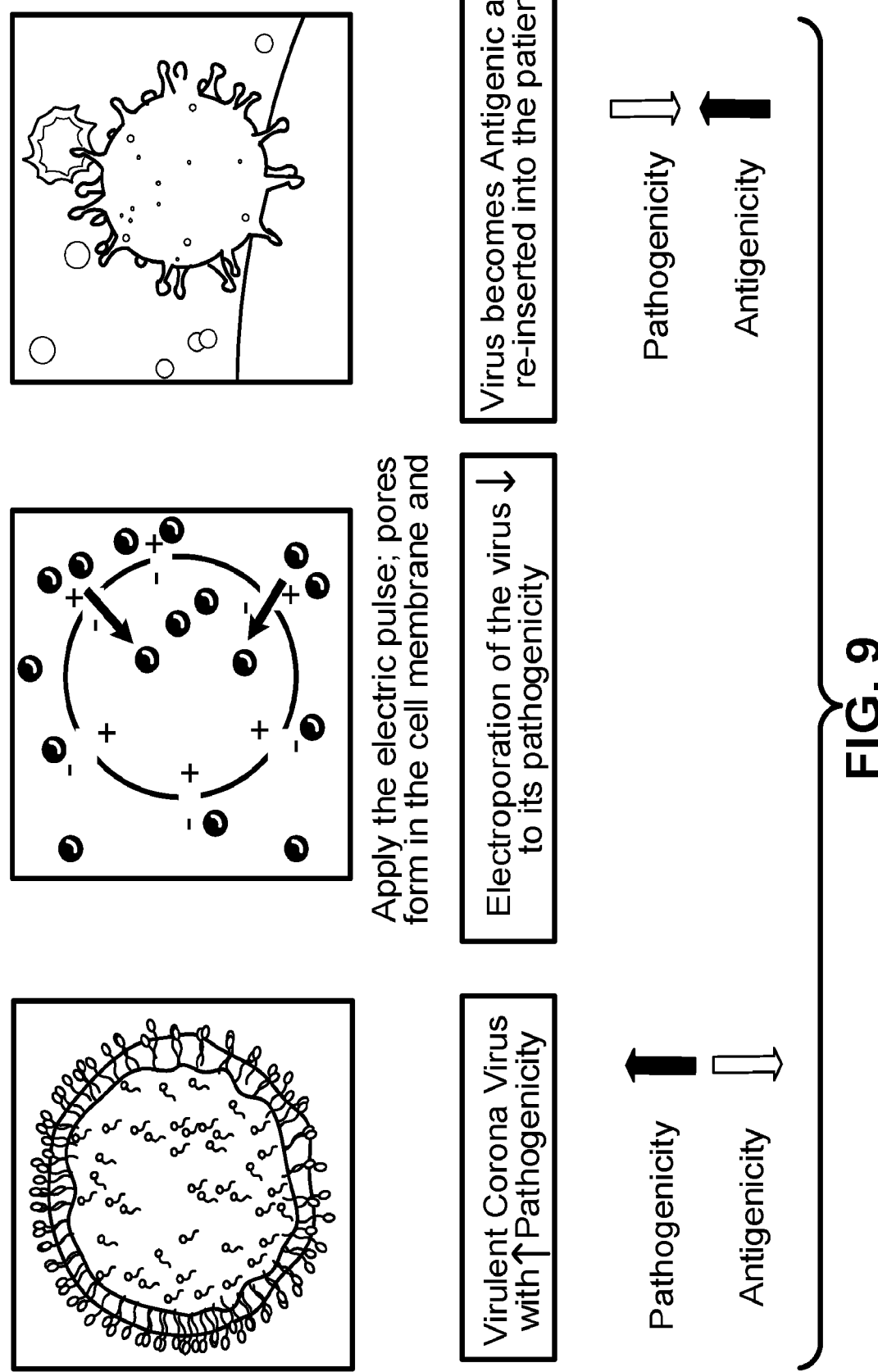
FIG. 9 shows the effects of electroporation to viruses.
Figure 10:
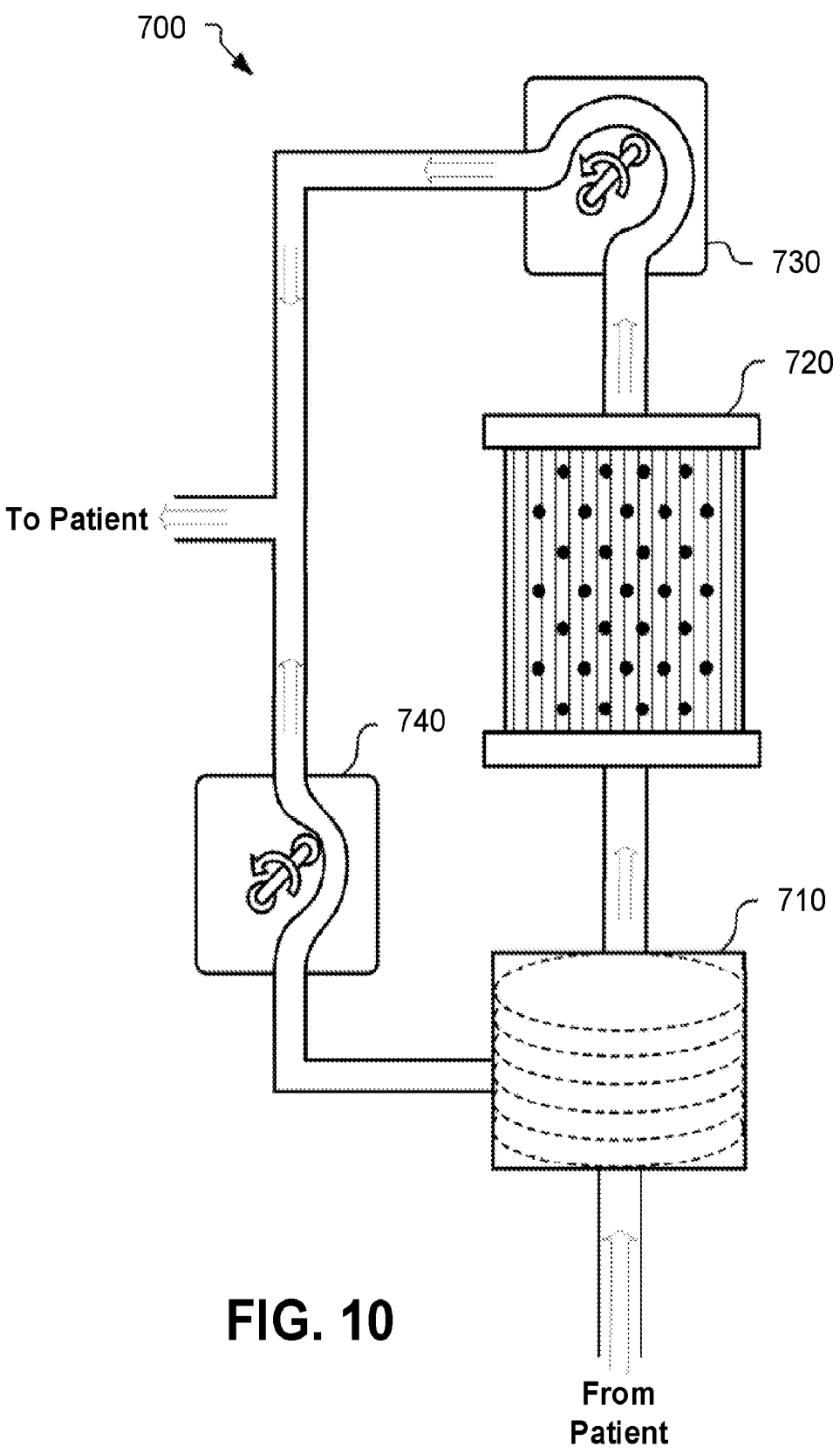
FIG. 10 is a schematic diagram of an example blood treatment system in accordance with some embodiments.

Referring to FIGS. 9 and 10, the blood treatment system 700 can be used to obtain virus free blood products. The blood treatment system 700 includes a blood product separator 710, an electroporation chamber 720, a first pump 730, and a second pump 740.

In operation, blood (that may include viruses) from a patient is channeled into the blood product separator 710. In the blood product separator 710 the blood is separated into two components: (i) blood containing cells and (ii) filtered plasma water containing viruses. The blood containing cells is channeled to the second pump 740 and returned to the patient. The filtered plasma water containing viruses is channeled to the electroporation chamber 720 for sterilization before being returned to the patient.

In the electroporation chamber 720, pulsed electric fields are applied to viruses contained within the filtered plasma. The electroporation chamber 720 can include a chamber with several electrodes through which the blood would flow. Electroporation would disrupt the viral envelopes thereby decreasing their pathogenicity. The disrupted viral particles would then serve as antigenic material that could then prime the immune system (as described in FIG. 9). While this approach may not decrease the viral load in non-circulating tissue, a significant decrease in viremia from the use of the blood treatment system 700 would still be beneficial especially given the possibility to recruit the immune system.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A system for treatment of lung infections of a patient, the system comprising:
an endotracheal tube;
a first electrode that is advanceable along the endotracheal tube;
a second electrode configured for placement on an exterior chest wall of the patient;
a source of particulate aerosols, the source configured to introduce the particulate aerosols into airways of the patient via the endotracheal tube;
a power source configured to deliver energy to the first electrode that causes the first electrode to emit pulse electroporation fields; and a monitor configured to track airway pressure and to discontinue delivery of energy in response to a change in plateau or peak airway pressures.

2. The system of claim 1, wherein the particulate aerosols comprise humidified or conducting particles configured to enhance efficacy of the pulse electroporation fields.

3. The system of claim 1, wherein the first electrode is configured to be positioned near the carina of the patient.

4. The system of claim 1, wherein the power source is configured to deliver pulsed energy at a voltage between 1 kilovolt and 20 kilovolts and a pulse duration of about 1 millisecond.

5. The system of claim 1, wherein the source of particulate aerosols comprises an aerosolized fluid source configured to inject aerosolized liquid selected from saline and distilled water into the endotracheal tube.

6. The system of claim 1, wherein the second electrode comprises a pair of return electrodes dimensioned for placement on respective left and right chest walls of the patient.

7. The system of claim 1, wherein the first electrode includes a distal portion positionable adjacent a carina of the patient when advanced along the endotracheal tube.

8. The system of claim 1, wherein the power source comprises a pulsed direct-current field generator.

* * * * *